(12) United States Patent
Park et al.

(10) Patent No.: US 7,608,435 B2
(45) Date of Patent: Oct. 27, 2009

(54) MICROORGANISM PRODUCING 5'-XANTHYLIC ACID

(75) Inventors: Young-Hoon Park, Seongnam-si (KR); Jea-Young Chang, Anyang-si (KR); Jin-Nam Lee, Yongin-si (KR); Ki-Hoon Oh, Icheon-si (KR); Jeong-Hwan Kim, Seoul (KR); Yoon-Suk Oh, Yongin-si (KR); Jae-Ick Sim, Icheon-si (KR)

(73) Assignee: CJ Cheiljedang Corp., Seoul (KR)

( * ) Notice: Subject to any disclaimer, the term of this patent is extended or adjusted under 35 U.S.C. 154(b) by 298 days.

(21) Appl. No.: 10/582,166

(22) PCT Filed: Nov. 18, 2004

(86) PCT No.: PCT/KR2004/002993

§ 371 (c)(1),
(2), (4) Date: Jun. 8, 2006

(87) PCT Pub. No.: WO2005/056775

PCT Pub. Date: Jun. 23, 2005

(65) Prior Publication Data

US 2007/0141682 A1    Jun. 21, 2007

(30) Foreign Application Priority Data

Dec. 10, 2003  (KR) .................... 10-2003-0089714

(51) Int. Cl.
*C12N 1/00*  (2006.01)
*C12N 1/02*  (2006.01)
*C12N 1/12*  (2006.01)
*C12N 15/00*  (2006.01)
*C12P 1/00*  (2006.01)
*C12P 7/00*  (2006.01)

(52) U.S. Cl. .................... 435/92; 435/136; 435/243; 435/252.1; 435/261; 435/440; 435/822; 435/843

(58) Field of Classification Search .................... None
See application file for complete search history.

(56) References Cited

FOREIGN PATENT DOCUMENTS

| EP | 0350970 A1 | 2/1984 |
| EP | 1029926 A1 | 2/2000 |
| KR | 1-89980 A | 10/2001 |
| KR | 02-57470 A | 7/2002 |

*Primary Examiner*—David M. Naff
*Assistant Examiner*—Deborah K. Ware
(74) *Attorney, Agent, or Firm*—Birch, Stewart, Kolasch & Birch, LLP

(57) ABSTRACT

The invention relates to a microorganism, obtained by treating *Corynebacterium ammoniagenes* KCCM 10488 producing 5'-Xanthylic acid as parent strain with UV radiation and mutation Derivatives such as N-methyl-N'nitro-N-nitrosoguanidine (NTG), Having a resistance to 5-fluorotryptophan which enhances Biosynthesis of N5-N10-tetrahydrofolate used for transferring Two formyl group during the process of puring biosynthesis, making It possible to accumulate 5'xanthylic acid in culture medium at a high Yield and high concentration rate same period of fermentation.

2 Claims, No Drawings

MICROORGANISM PRODUCING 5'-XANTHYLIC ACID

TECHNICAL FIELD

The invention relates to a microorganism producing 5'-xanthylic acid. More particularly, the invention relates to a mutant strain of *Corynebacterium ammoniagenes* KCCM 10448, which is given a resistance to 5-fluorotryptophan, a metabolite analogue of tryptophan, in order to enhance purine biosynthesis, making it possible to enhance $N_5$, $N_{10}$-tetrahydrofolate involved in purine biosynthesis pathway, and to accumulate 5'-xanthylic acid in culture medium at a high yield and high concentration rate for same period of fermentation.

BACKGROUND ART

5'-xanthylic acid is an intermediate in the nucleic acid biosynthesis process, which is physiologically important in the body of animals and plants, used in food, medical supplies and other various field. Thus, inventors of the invention developed a mutant strain having a resistance to 5-fluorotryptophan, from a known strain *Corynebacterium ammoniagenes* KCCM 10448 also developed by inventors of the invention, producing 5'-xanthylic acid at a high yield and high concentration rate by a direct fermentation method.

5'-xanthylic acid is an intermediary product of purine nucleotide biosynthesis process and important material for producing 5'-guanylic acid. A widely used method to produce 5'-guanylic acid having fineness and high quality is microorganism fermentation method which produces 5'-xanthylic acid first and converts it into 5'-guanylic acid enzymatically, therefore, to produce 5'-guanylic acid, corresponding amount of 5'-xanthylic acid is necessary. Conventional methods to produce 5'-xanthylic acid are chemosynthesis, deaminization of 5'-guanylic acid which is produced as a result of decomposition of ribonucleic acid in yeast, a fermentation method to add xanthine as precursor material in fermenting medium, a fermentation method to use a mutant strain of microorganism, a method to add antibiotic material (JP 1477/42 and JP 20390/44), a method to add surfactant (JP 3825/42 and JP 3838/42) and so on. Among these, a direct fermentation method of 5'-xanthylic acid by a mutant strain of microorganism is quite advantageous in terms of industrial aspect. Thus, we inventors developed a mutant strain with increased productivity of 5'-xanthylic acid, by modifying the existing character of *Corynebacterium ammoniagenes* KCCM 10448 into the character of producing 5'-xanthylic acid at a large yield rate.

DISCLOSURE OF THE INVENTION

Technical Problem

The biosynthesis pathway for producing XMP is very complicated, and the reaction in which various amino acids and coenzymes participate continues. Especially, $N_5$, $N_{10}$-tetrahydrofolate participates in two steps among six steps reactions from PRPP (Phosphoribosylpyrophosphate) to XMP, and plays a role in transferring formyl group to each precursor. Meanwhile, p-aminobenzoate, synthesized from chorismate, is necessary for biosynthesis of $N_5,N_{10}$-tetrahydrofolate. Chorismate is an intermediary product in tryptophan biosynthesis process and the inventors thought that enhancement of producing chorismate results in enhancement of producing $N_5$, $N_{10}$-tetrahydrofolate. Thus, the inventors examined a mutant strain, which is given a resistance to 5-fluorotryptophan, a metabolite analogue of tryptophan, in order to enhance purine biosynthesis, and which enhances biosynthesis of chorismate and increases $N_5,N_{10}$-tetrahydrofolate, and found out that a mutant strain having a resistance to 5-fluorotryptophan is very effective and can produce 5'-xanthylic acid at a high yield and high concentration rate by a direct fermentation method than prior art, and accomplished in this invention.

Technical Solution

Now, a method for separating and taking the microorganism of the present invention is explained in detail.

The microorganism of the invention, *Corynebacterium ammoniagenes* CJXFT 0301 (KCCM-10530) is obtained by treating *Corynebacterium ammoniagenes* KCCM 10448 as parent strain with UV radiation and mutation derivatives such as N-methy-N'-nitro-n-nitrosoguanidine (NTG) according to ordinary procedure, and selecting a mutant strain among these which can grow in the culture medium (glucose 20 g/L, potassium phosphate monobasic 1 g/L, potassium phosphate dibasic 1 g/L, urea 2 g/L, ammonium sulfate 3 g/L, magnesium sulfate 1 g/L, calcium chloride 100 mg/L, ferrous sulfate 20 mg/L, manganese sulfate 10 mg/L, zinc sulfate 10 mg/L, biotin 30 µg/L, thiamine hydrochloride 0.1 mg/L, copper sulfate 0.8 mg/L, adenine 20 mg/L, guanine 20 mg/L, pH 7.2) which different concentration levels of fluorotryptophan (10, 20, 50, 70, 100, 200 mg/L) is added into. In the procedure, 0~200 mg/L fluorotryptophan was added into the medium. Parent strain showed a resistance up to 20 mg/L fluorotryptophan but no growth was observed at the concentration level above 50 mg/L, therefore the inventors separated a strain which can grow in 10 mg/L fluorotryptophan, named CJXFT 0301, and deposited it under Budapest Treaty to the Korean Culture Center of Microorganisms on Nov. 25, 2003 with accession Number KCCM 10530.

The biochemical characteristic of the novel mutant strain CJXFT 0301 of the invention is shown in the following Table 1. According to the Table 1, the microorganism of the invention can grow in the medium which 100 mg/L fluorotryptophan was added into.

TABLE 1

| Strain | Fluorotryptophan Concentraion (mg/L) | | | | | | |
|---|---|---|---|---|---|---|---|
| | 0 | 10 | 20 | 50 | 70 | 100 | 200 |
| KCCM 10448 | +++ | ++ | + | − | + | − | − |
| CJXFT 0301 | +++ | +++ | +++ | +++ | ++ | + | − |

The medium was fermented at 30° C. for 5 days.
+: growth,
−: no growth

ADVANTAGEOUS EFFECTS

The invention adopted *Corynebacterium ammoniagenes* KCCM 10448 as parent strain and treated it UV radiation or mutation derivatives such as N-methy-N'-nitro-n-nitrosoguanidine (NTG) according to ordinary procedure, to obtain a mutant strain. The mutant strain is given a resistance to 5-fluorotryptophan, in order to enhance biosynthesis of $N_5,N_{10}$-tetrahydrofolate used for transferring two formyl group during the process of purine biosynthesis, and the strain has an effect on accumulating 5'-xanthylic acid in culture medium at a high yield and high concentration rate for same period of fermentation.

MODE FOR CARRYING OUT THE INVENTION

Example 1

Used strains: *Corynebacterium ammoniagenes* KCCM 10448, *Corynebacterium ammoniagenes* CJXFT 0301 (KCCM 10530)

Seed medium: glucose 30 g/L, peptone 15 g/L, yeast extract 15 g/L, sodium chloride 2.5 g/L, urea 3 g/L, adenine 150 mg/L, guanine 150 mg/L, pH 7.2

Fermentation medium: (1) A medium: glucose 60 g/L, magnesium sulfate 10 g/L, ferrous sulfate 20 mg/L, zinc sulfate 10 mg/L, manganese sulfate 10 mg/L, adenine 30 mg/L, guanine 30 mg/L, biotin 100 μg/L, copper sulfate 1 mg/L, thiamine hydrochloride 5 mg/L, calcium chloride 10 mg/L, pH 7.2

(2) B medium: potassium phosphate monobasic 10 g/L, potassium phosphate dibasic 10 g/L, urea 7 g/L, ammonium sulfate 5 g/L Fermentation method: 5 mL of the seed medium was poured into a test tube having diameter of 18 mm and sterilized under pressure according to the common methods. After the sterilization, *Corynebacterium ammoniagenes* KCCM 10448 and *Corynebacterium ammoniagenes* CJXFT 0301 were seeded into respectively and it was cultured with shaking at 180 rpm, 30° C. for 18 hours. The resultant was used as seed culture. Then, as fermentation medium, A medium and B medium were sterilized separately under pressure according to the common methods and 29 mL of A medium and 10 mL of B medium were respectively poured into sterilized 500 mL-Erlenmeyer flask for shaking and 1 mL of the above-mentioned seed culture was seeded into and fermented at 200 rpm, 30° C. for 90 hours. After the fermentation was completed, the amount of accumulation of 5'-xanthylic acid in the medium showed that the amount in KCCM 10448 was 25.4 g/L and the amount in CJXFT 0301 was 28.6 g/L. (The concentration of accumulated 5'-xanthylic acid is given by 5'-sodium xanthate.7H$_2$O.)

Example 2

Used strains: same as example 1.

Primary seed medium: same as the seed medium of example 1.

Secondary seed medium: glucose 60 g/L, potassium phosphate monobasic 2 g/L, potassium phosphate dibasic 2 g/L, magnesium sulfate 1 g/L, ferrous sulfate 22 mg/L, zinc sulfate 15 mg/L, manganese sulfate 10 mg/L, copper sulfate 1 mg/L, calcium chloride 100 mg/L, biotin 150 μg/L, adenine 150 mg/L, guanine 150 mg/L, thiamine hydrochloride 5 mg/L, antifoaming agent 0.6 mL/L, pH 7.2

Fermentation medium: glucose 151 g/L, phosphoric acid 32 g/L, potassium hydroxide 25 g/L, adenine 198 mg/L, guanine 119 mg/L, ferrous sulfate 60 mg/L, zinc sulfate 42 mg/L, manganese sulfate 15 mg/L, copper sulfate 2.4 mg/L, alaniate 22 mg/L, NCA 7.5 mg/L, biotin 0.4 mg/L, magnesium sulfate 15 g/L, cystinate 30 mg/L, histidinate 30 mg/L, calcium chloride 149 mg/L, thiamine hydrochloride 15 mg/L, antifoaming agent 0.7 mL/L, CSL 27 mL/L, tuna extract 6 g/L, pH 7.3

Primary seed culture: 50 mL of the primary seed medium was poured into 500 mL-Erlenmeyer flask for shaking and sterilized under pressure at 121° C. for 20 minutes. After cooling, *Corynebacterium ammoniagenes* KCCM 10448 and *Corynebacterium ammoniagenes* CJXFT 0301 were seeded into respectively and it was cultured with shaking at 180 rpm, 30° C. for 24 hours.

Secondary seed culture: The secondary seed medium was poured into 5 L-experimental fermentation baths (2 L each) and sterilized under pressure at 121° C. for 20 minutes. After cooling, 50 mL of the above primary seed culture was seeded and cultured with the air supply of 0.5 vvm, at 900 rpm, 31° C., for 24 hours. During the culturing process, the pH level of the medium was kept at 7.3 with adjusting by ammonia solution.

Fermentation method: The fermentation medium was poured into 30 L-experimental fermentation baths (8 L each) and sterilized under pressure at 121° C. for 20 minutes. After cooling, the above secondary seed culture was seeded into (1.5 L each) and cultured with the air supply of 1 vvm, at 400 rpm, 33° C. Whenever the residual sugar level drops below 1% during the culturing process, sterilized glucose was supplied and the total sugar level in the fermentation medium was kept at 30%. During the culturing process, the pH level of the medium was kept at 7.3 with adjusting by ammonia solution and the process took 80 hours. After the fermentation was completed, the amount of accumulation of 5'-xanthylic acid in the medium showed that the amount in KCCM 10448 was 145.2 g/L and the amount in CJXFT 0301 was 155.4 g/L. (The concentration of accumulated 5'-xanthylic acid is given by 5'-sodium xanthate.7H$_2$O.)

What is claimed is:

1. An isolated microorganism CJXFT 0301 (Accession Number: KCCM-10530) producing 5'-xanthylic acid, which is a mutant strain of *Corynebacterium ammoniagenes* having a resistance to 5-fluorotryptophan.

2. A method of producing 5'-xanthylic acid using the isolated microorganism of claim 1.

* * * * *